US008528416B2

(12) United States Patent
Lee et al.

(10) Patent No.: US 8,528,416 B2
(45) Date of Patent: Sep. 10, 2013

(54) APPARATUS FOR TESTING TENSILE STRENGTH UNDER HIGH TEMPERATURE CONDITION AND UNIT FOR MEASURING ELONGATION PROVIDED IN THE SAME

(75) Inventors: Bong Jae Lee, Seoul (KR); Yong Ho Yoo, Incheon (KR); Heung Youl Kim, Seoul (KR); Hyung Jun Kim, Gyeonggi-Do (KR); Kyung Hoon Park, Seoul (KR)

(73) Assignee: Korea Institute of Construction Technology, Gyeonggi-Do (KR)

( * ) Notice: Subject to any disclaimer, the term of this patent is extended or adjusted under 35 U.S.C. 154(b) by 216 days.

(21) Appl. No.: 12/947,173

(22) Filed: Nov. 16, 2010

(65) Prior Publication Data

US 2011/0126635 A1 Jun. 2, 2011

(30) Foreign Application Priority Data

Nov. 27, 2009 (KR) .......................... 10-2009-0115519
Dec. 16, 2009 (KR) .......................... 10-2009-0125725

(51) Int. Cl.
*G01N 3/08* (2006.01)

(52) U.S. Cl.
USPC .......................................................... 73/826

(58) Field of Classification Search
USPC ............................................................ 73/826
See application file for complete search history.

(56) References Cited

U.S. PATENT DOCUMENTS

| 2,375,034 | A | * | 5/1945 | Semchyshen | ................... 374/50 |
| 2,534,980 | A | * | 12/1950 | Lubahn | ........................... 374/49 |
| 4,425,810 | A |   | 1/1984 | Simon et al. | |
| 6,112,589 | A | * | 9/2000 | Tressler et al. | ................. 73/160 |

OTHER PUBLICATIONS

S.A.Maloy et al, "The High Temperature Tensile Properties of Ferritic-Martensitic and Austenitic Steels After Irradiation in an 800 MEV Proton Beam" appears in Seventh Information Exchange Meeting on Actinide and Fission Product Partitioning and Transmutation, issued on Oct. 14-16, 2002, p. 669-678.
ING.BIRGIT REHMER, "Tensile Test Facility for Temperatures up to 1900 °C", appears in Unique Test Facilities, Chapter 5:Materials Engineering, issued on Sep. 9, p. 1-2.

* cited by examiner

*Primary Examiner* — Harshad R Patel
*Assistant Examiner* — Octavia D. Hollington
(74) *Attorney, Agent, or Firm* — J.C. Patents (57) ABSTRACT

Provided are an apparatus for testing a tensile strength under a high temperature condition and a unit for measuring elongation provided in the same. The apparatus for testing a tensile strength under a high temperature condition includes a base frame part, a test sample loader and a cylinder part connected to the base frame part and applying a tensile force to a test sample, and a heater for forming a high temperature condition to the test sample. The unit for measuring elongation includes a movable frame, a vertical bar, and a measurement head part connected to the vertical bar to measure elongation of the test sample and blocking heat from the heater. Therefore, since a tensile strength and elongation of the test sample can be measured under a high temperature condition, it is possible to recognize deformation characteristics of a material due to a fire and prevent deformation of or damage to the elongation measurement unit even under the high temperature condition, improving durability and reliability of the apparatus.

6 Claims, 9 Drawing Sheets

APPARATUS FOR TESTING TENSILE STRENGTH UNDER HIGH TEMPERATURE CONDITION AND UNIT FOR MEASURING ELONGATION PROVIDED IN THE SAME

CROSS-REFERENCE TO RELATED APPLICATION

This application claims the priority benefit of Korea application serial no. 10-2009-0115519, filed on Nov. 27, 2009 and Korea application serial no. 10-2009-0125725, filed on Dec. 16, 2009. The entirety of each of the above-mentioned patent applications is hereby incorporated by reference herein and made a part of specification.

BACKGROUND

1. Field

The present invention relates to an apparatus for testing a tensile strength under a high temperature condition and a unit for measuring elongation provided in the same, and more particularly, to an apparatus for measuring a tensile strength and elongation of a test sample under a high temperature condition.

2. Description of the Related Art

In general, a fire generated in a closed concrete structure may cause serious damage to the concrete structure. In particular, a fire generated in an enclosure such as an underground space increases a temperature to 1000° C. or more within several minutes after the fire and then is maintained for a long time. In this case, a spalling failure may occur, causing damage to concrete, which is a construction material of the concrete structure.

The spalling failure means that, when a large amount of heat of 400° C. or more is continuously applied to the concrete, moisture confined in the concrete explosively bursts out, causing damage to the concrete surface and melting reinforcing bars in the concrete so that the structure easily collapses.

While it has been known that the concrete structure has material characteristics such as low thermal conductivity and a non-combustible property, the structural performance may abruptly decrease due to the spalling failure generated from the concrete surface under a high temperature exposure circumstance such as a fire.

When the spalling failure occurs, the reinforcing bars in the concrete are also exposed to a high temperature and directly affected by the heat. Therefore, in order to measure structural deformation of the reinforcing bars due to the fire, a test for measuring strain and elongation of the reinforcing bars under the high temperature condition is essential.

However, since a conventional tensile strength test apparatus and a conventional elongation measuring apparatus are configured without consideration of the high temperature condition, it is impossible to accurately measure variation in tensile strength, strain and elongation of a test sample such as a reinforcing bar upon occurrence of a fire.

In addition, in the case of an apparatus for measuring elongation of a test sample, since the apparatus is not configured to test without affection by the heat under the high temperature condition, when the apparatus for testing a tensile strength is under the high temperature condition, the apparatus may be affected by the heat to be damaged or make accurate measurement difficult.

SUMMARY

In order to solve the problems, the present invention is directed to an apparatus for testing a tensile strength capable of measuring a tensile strength and elongation of a test sample under a high temperature condition.

The present invention is also directed to a unit for measuring elongation, which is not affected by heat during a test process.

According to an exemplary aspect, there is provided an apparatus for testing a tensile strength under a high temperature condition, which measures a tensile strength or elongation of a test sample, including: a high temperature tension unit for applying a tensile force to the test sample and selectively forming a high temperature condition to the test sample; and an elongation measurement unit integrally or separately formed with the high temperature tension unit to measure elongation of the test sample by the high temperature tension unit.

Here, the high temperature tension unit may include a base frame part; a tensile force applying part for applying a tensile force to the test sample; and a heater connected to the base frame part and forming a high temperature condition to the test sample.

In addition, the base frame part may include a surface plate, four support masts extending upward from the surface plate, and a fixing mount connected to the support masts to move vertically.

Further, the tensile force applying part may include a test sample loader having an upper test sample loader connected to the fixing mount and a lower test sample loader connected to the surface plate and fixing and tensing the test sample between the upper and lower test sample loaders, and a cylinder part for moving the test sample loader.

Furthermore, the heater may include a heater body connected to the base frame part and formed to pass the test sample therethrough; a plurality of hot-wires installed in the heater body; and a heat blocking material installed in the heater body and limiting discharge of the heat to the exterior.

In addition, the heater body may be pivotally connected to the base frame part.

Further, the heater body may be configured to be separated into left and right halves, and have an insertion slit through which a measurement bar is inserted to measure elongation of the test sample.

According to another exemplary aspect, there is provided a unit for measuring elongation, which is provided in an apparatus for measuring a tensile strength or elongation of a test sample under a high temperature condition, including: a movable frame; a vertical bar extending upward from the movable frame; and a measurement head part vertically movably connected to the vertical bar, and configured to measure elongation of the test sample and prevent transfer of heat to the movable frame or the vertical bar.

Here, the measurement head part may include a head body vertically movably connected to the vertical bar; two measurement bars vertically movably connected to the head body and contacting the test sample; a cooler installed at the measurement bar and cooling the measurement bars; and a guide bar installed at the measurement head part to block heat applied to the measurement head part.

In addition, the cooler may cool the measurement bar using cooling water supplied from the exterior.

Further, the heat blocking part may be formed of a non-combustible fiber or a fireproof fiber.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the aspects of the invention.

DETAILED DESCRIPTION

The invention is described more fully hereinafter with reference to the accompanying drawings, in which exemplary embodiments of the invention are shown. This invention may, however, be embodied in many different forms and should not be construed as limited to the exemplary embodiments set forth herein. Rather, these exemplary embodiments are provided so that this disclosure is thorough, and will fully convey the scope of the invention to those skilled in the art.

Hereinafter, an apparatus for testing a tensile strength in a high temperature condition and a unit for measuring elongation provided in the same in accordance with the present invention will be described with reference to the accompanying drawings in detail.

The present invention is directed to an apparatus for measuring a tensile strength and elongation of a test sample under a high temperature condition, which obeys general tensile test conditions.

For example, the size of the test sample of the present invention must satisfy a test standard of KS B 0801 (1981-2002): Metal Material Tensile Test, and high temperature heating and tensile test conditions of a reinforcing bar having a maximum size (diameter Φ32×length 560 mm).

In addition, a heating temperature condition of a test sample must satisfy test standards, for example, ISO834-1 (1999: Fire-Resistance Tests-Elements of Building Construction-Part 1), KS F 2257-1 (2005: Fireproof Test Method of Construction Member—General Requirements), BS 476 (1987: Fire Test on Building Materials and Structures—Part 20), UL 10B (Fire Test of Door Assemblies), UL 10C (Positive Pressure Fire Tests of Door Assemblies) or UL 263 (Fire Tests of Building Construction and Materials).

FIGS. 1 to 9 show an apparatus for testing a tensile strength under a high temperature condition and a unit for measuring elongation provided in the same in accordance with an exemplary embodiment of the present invention.

Figure 1:
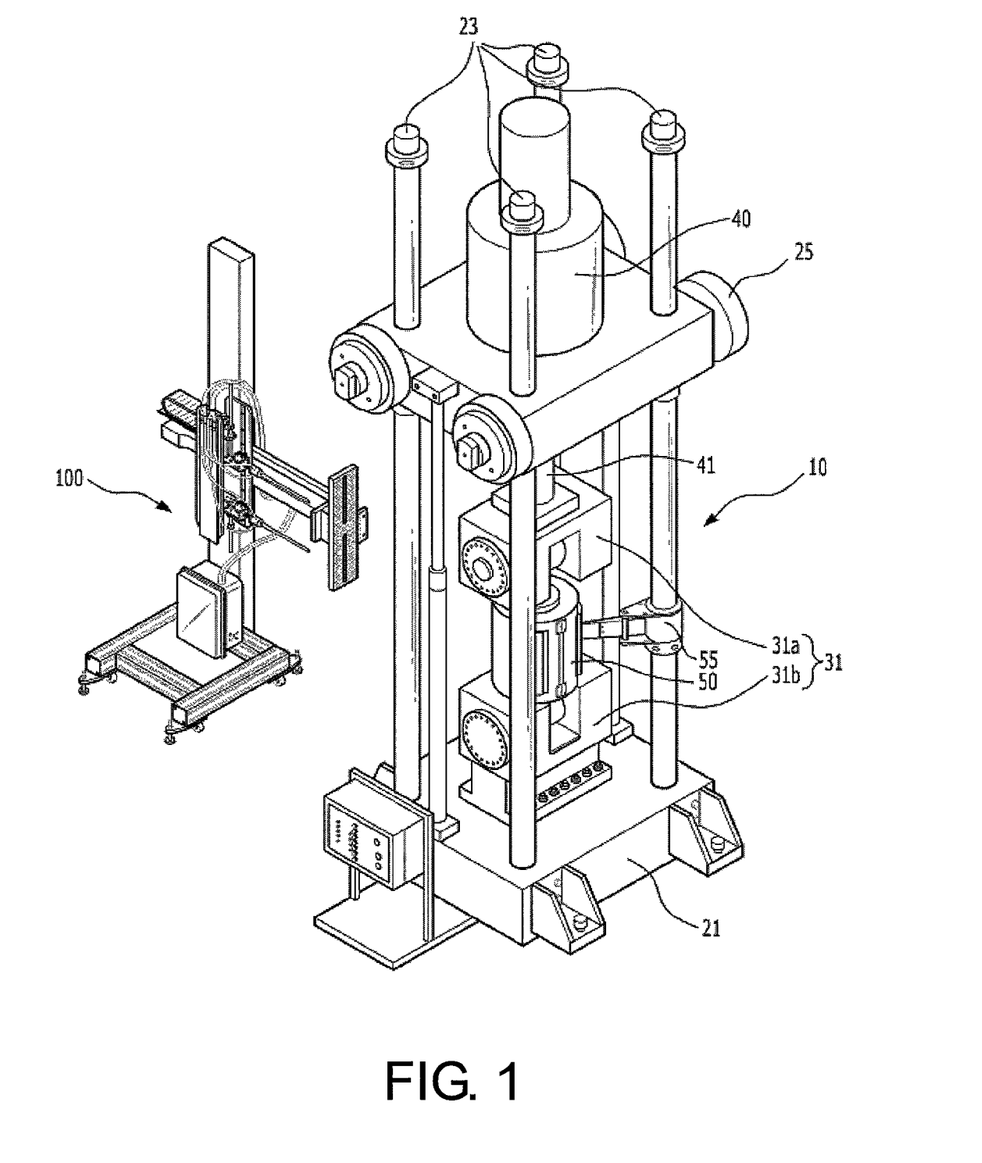
FIG. 1 is a perspective view of an apparatus for testing a tensile strength under a high temperature condition and a unit for measuring elongation provided in the same in accordance with an exemplary embodiment of the present invention.

As shown in FIG. 1, the apparatus for testing a tensile strength in a high temperature condition in accordance with the present invention includes a high temperature tension unit 10 for applying a tensile force to a test sample t under a high temperature condition, and an elongation measurement unit 100 for measuring elongation of the test sample t tensed by the high temperature tension unit 10.

The high temperature tension unit 10 includes a base frame part 20 acting as a base support body of the high temperature tension unit 10. The base frame part 20 includes a surface plate 21 installed at a flat bottom, and four support masts 23 installed at the surface plate 21 in a vertical upward direction.

The support masts 23 function to support a fixing mount 25 on which a tensile force applying part 30 is installed, which is to be described. The fixing mount 25 is connected to the support mast 23 to vertically move along the support mast 23.

Therefore, when the fixing mount 25 is vertically moved to set a proper position, the fixing mount 25 is securely fixed to the support mast 23 to prevent movement of the fixing mount 25.

The tensile force applying part 30 is installed at the fixing mount 25 to apply a tensile force to the test sample t. The tensile force applying part 30 includes a test sample loader 31 divided into upper and lower parts to be installed at a lower surface of the fixing mount 25 and an upper surface of the surface plate 21, respectively.

The test sample loader 31 functions to grip the test sample t. The upper test sample loader 31a is connected to the fixing mount 25, and the lower test sample loader 31b is connected to the surface plate 21. The test sample t is connected between the upper test sample loader 31a and the lower test sample loader 31b to be pulled, testing a tensile strength of the test sample t.

A vice part 33 is installed at the test sample loader 31 to securely fix the test sample t. In addition, a cylinder part 40 is installed at the fixing mount 25. The cylinder part 40 may be constituted by a hydraulic cylinder, etc., to pull the upper test sample loader 31a upward.

Figure 2:
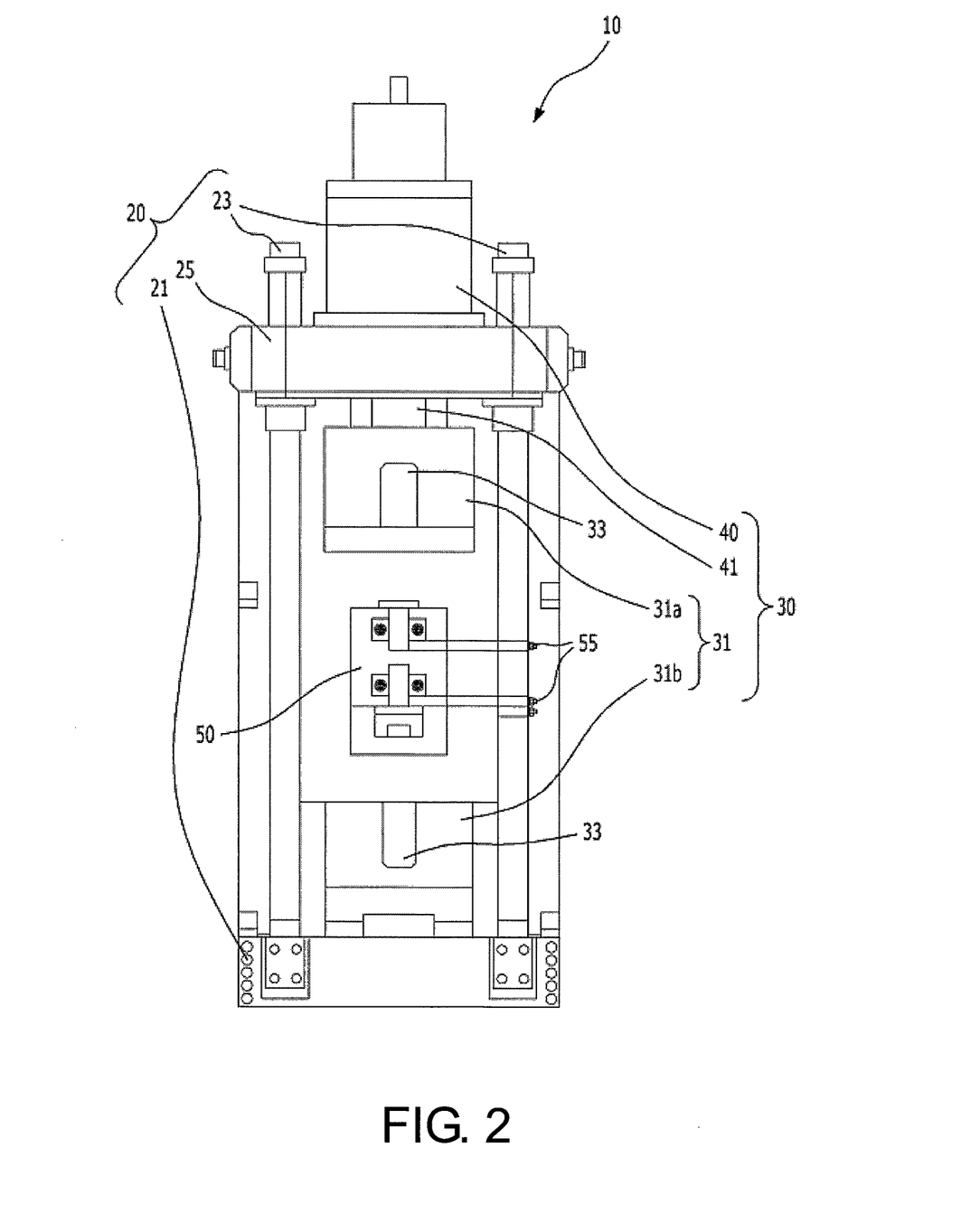
FIG. 2 is a front view of FIG. 1.
Figure 3:
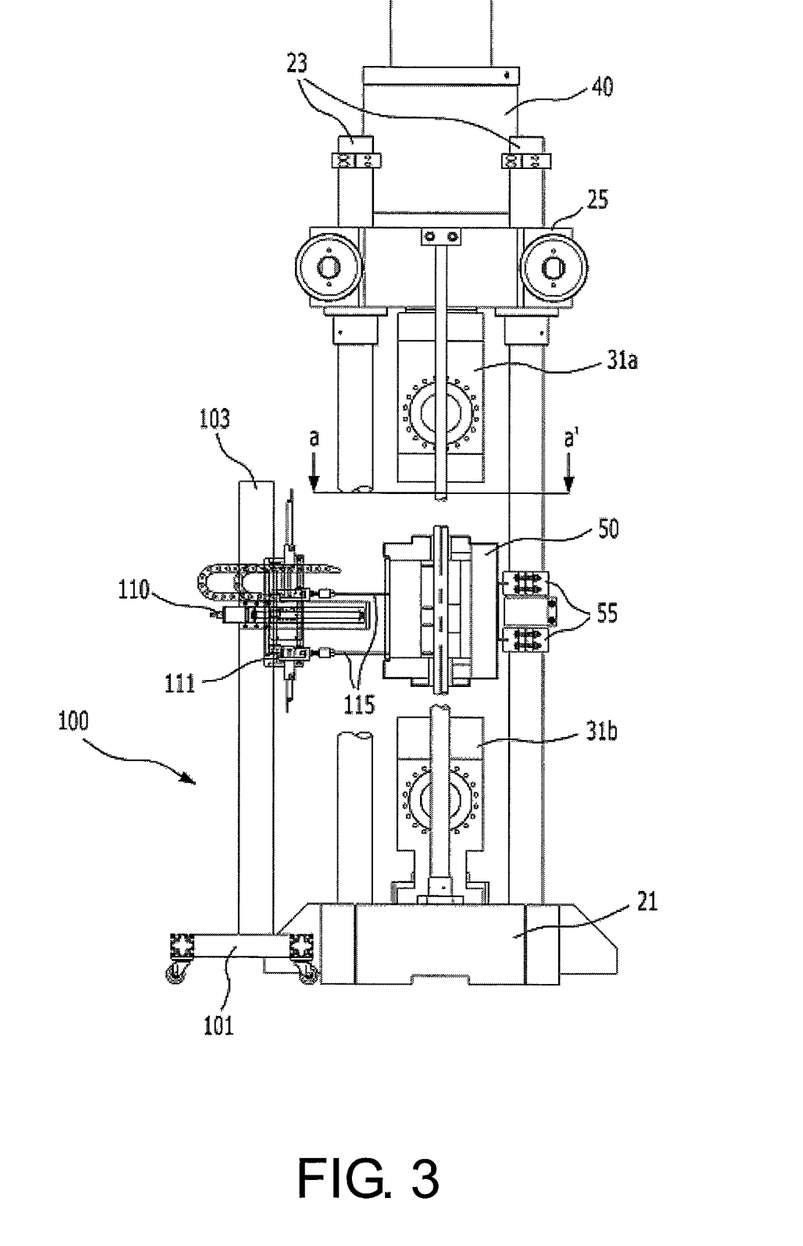
FIG. 3 is a side view of FIG. 1.

In addition, as shown in FIG. 2, the cylinder part 40 includes a cylinder rod 41 to support the upper test sample loader 31a. The upper test sample loader 31a can be vertically moved along the cylinder rod 41. Therefore, the cylinder part 40 pulls the upper test sample loader 31a upward using the cylinder rod 41 to apply a tensile force to the test sample t.

Figure 4:
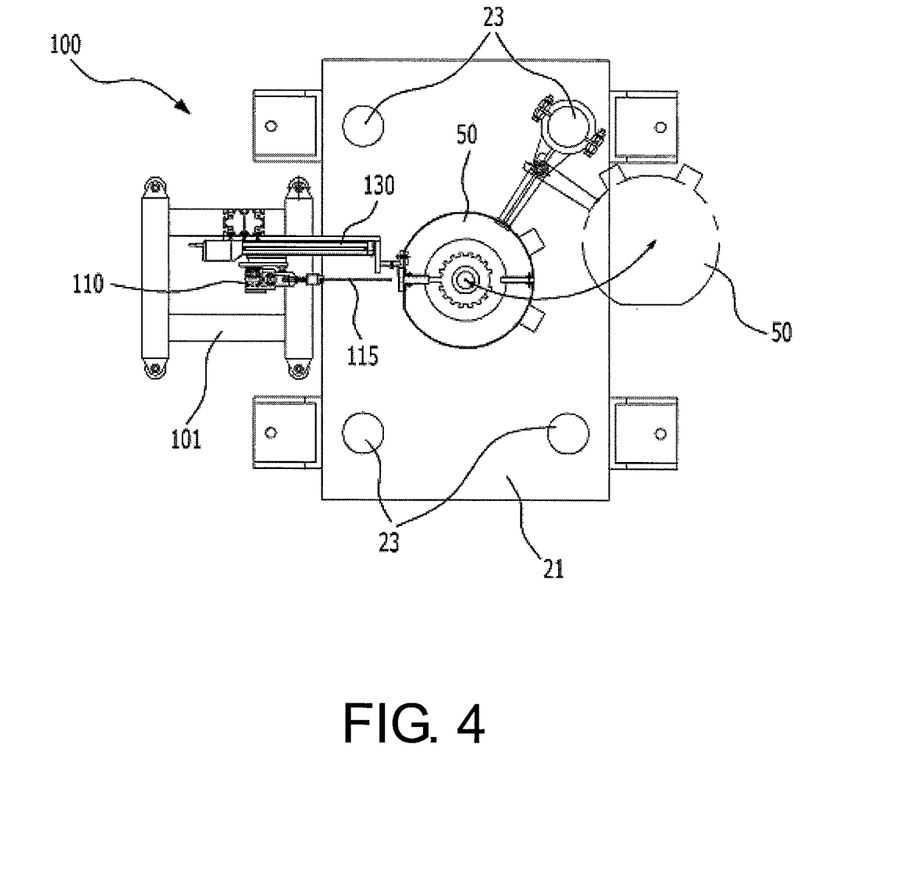
FIG. 4 is a cross-sectional view taken along line a-a' of FIG. 3.

A heater 50 is connected to any one of the support masts 23 to form a high temperature condition around the test sample t. As shown in FIG. 4, the heater 50 is pivotally connected to the support mast 23 so that the tensile strength can be measured in both a high temperature condition and a normal temperature condition.

Figure 5:
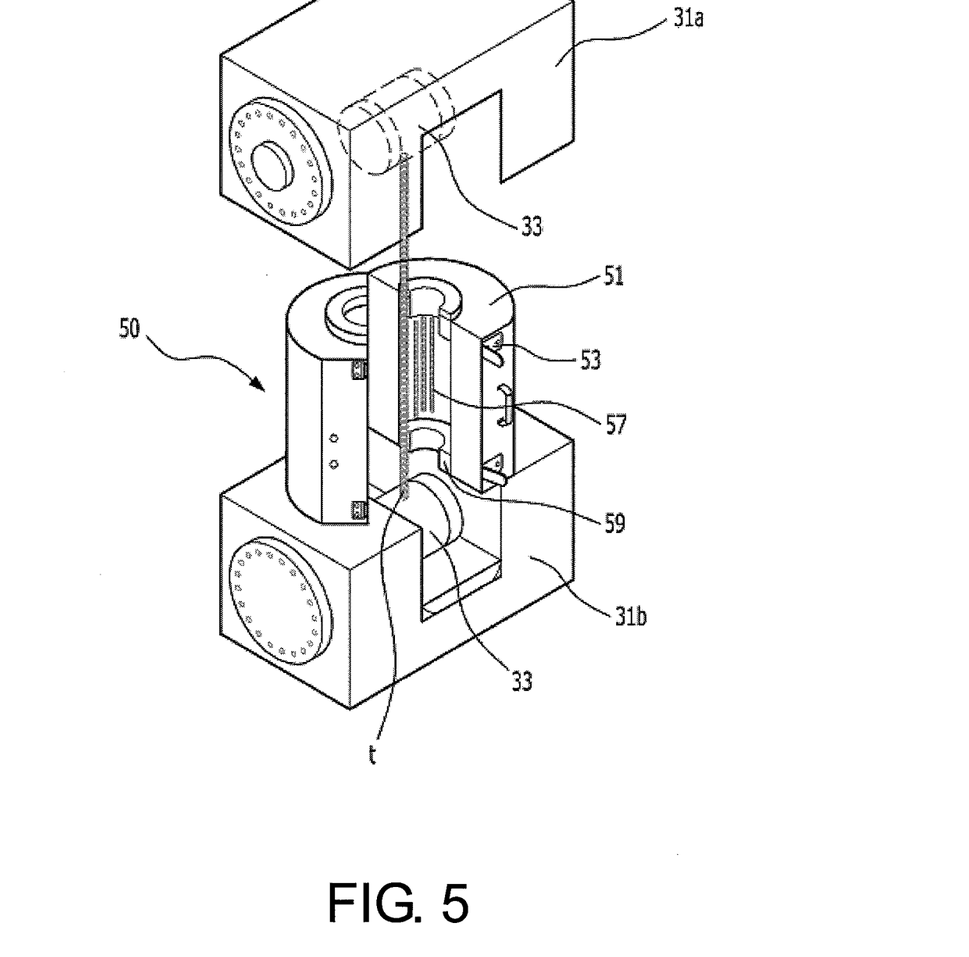
FIG. 5 is a partial perspective view of an open state of a heater body of the apparatus for testing a tensile strength under a high temperature condition in accordance with the present invention.

As shown in FIG. 5, the heater 50 includes a heater body 51 having a cylindrical shape. Here, the heater body 51 may be configured to be laterally separated into halves.

Grooves are formed in the laterally separated halves of the heater body 51 so that the test sample t can pass therethrough. In addition, connection clips 53 are installed at the halves of the heater body 51 to couple the halves of the heater body 51 to each other.

Figure 6:
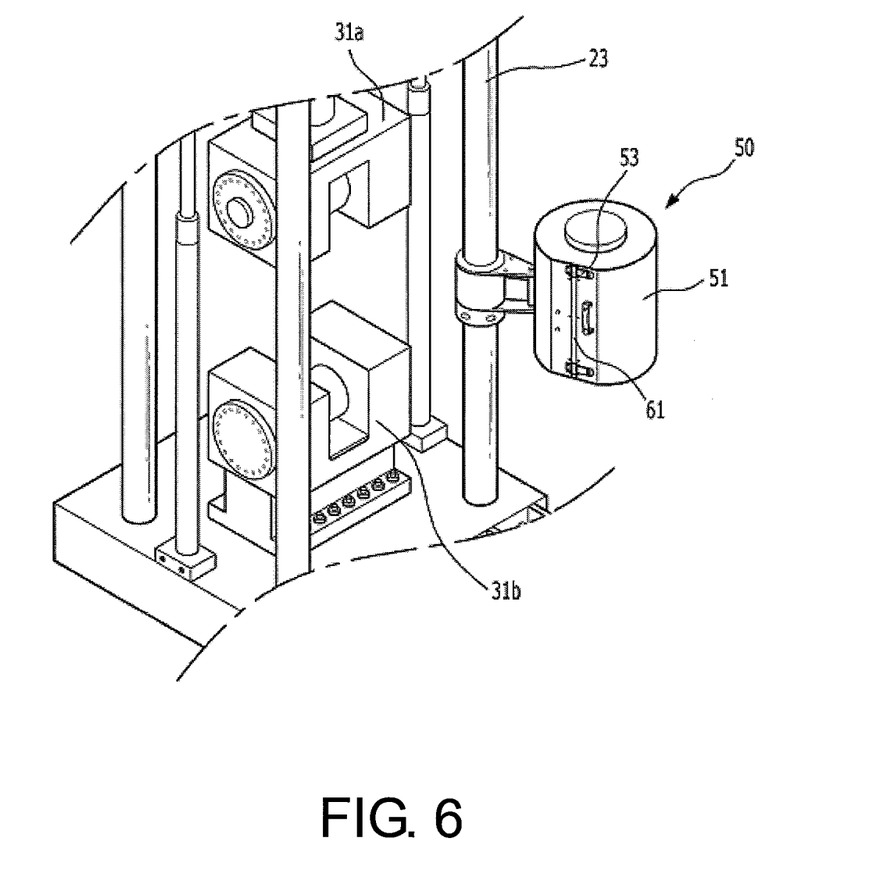
FIG. 6 is a partial perspective view of a state in which the heater body of the apparatus for testing a tensile strength under a high temperature condition in accordance with the present invention is rotated to the exterior.

The heater body 51 is pivotally connected to the support mast 23 by a pivot member. Accordingly, when a tensile strength is measured at a normal temperature, as shown in FIG. 6, the heater body 51 may be pivoted to exit the high temperature tension unit 10.

A plurality of hot-wires 57 are installed in the heater body 51, and an insulating material 59 formed of a ceramic material is filled in the heater body 51 to prevent discharge of heat in the heater body 51 to the exterior.

In addition, an insertion slit 61 through which a measurement rod 115 to be described below is inserted is formed at a portion of the heater body 51 at which the separated halves are coupled to each other. Further, a plurality of temperature measurement sensors (not shown) may be installed in the heater 50 to set an accurate temperature condition.

The heater 50 can provide various fire conditions. That is, the heater 50 of the present invention is controlled by an external controller to implement all important fire curves used in a general fire test. Accordingly, the heater 50 can provide fire conditions according to characteristics of the fire curve input by a user.

The apparatus for testing a tensile strength under a high temperature condition in accordance with the present invention includes a unit 100 for measuring elongation, which is separately provided from the high temperature tension unit 10. The elongation measurement unit 100 is a unit for measuring elongation of a test sample tensed by the high temperature tension unit 10.

Figure 7:
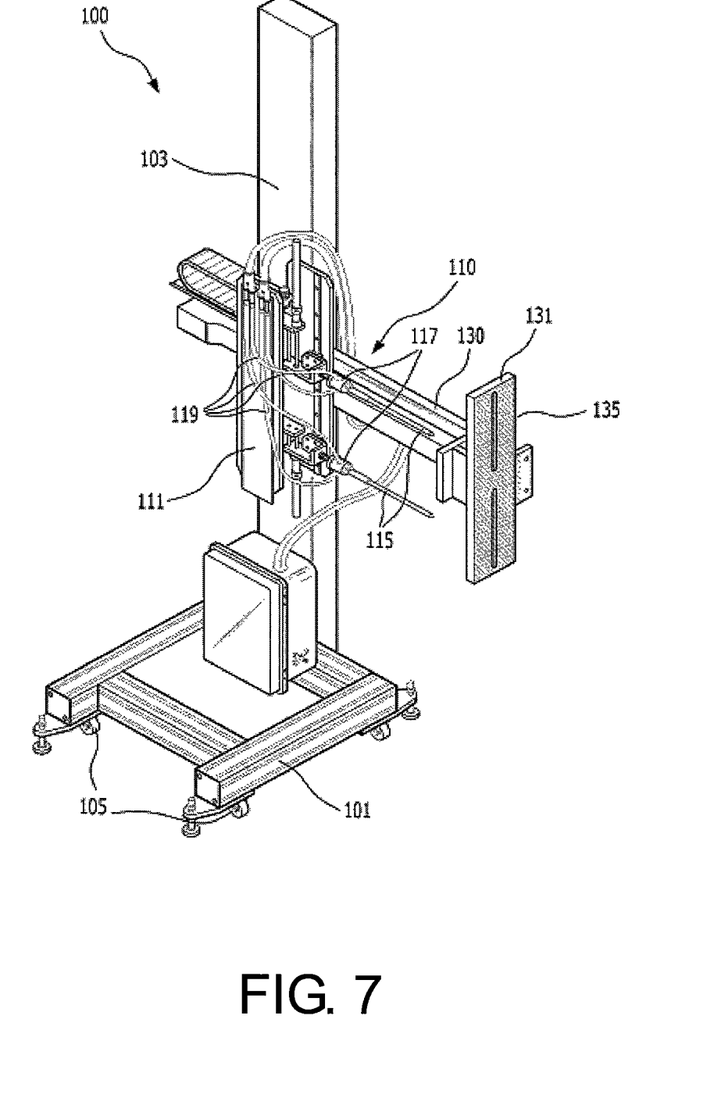
FIG. 7 is a perspective view of a unit for measuring elongation in accordance with an exemplary embodiment of the present invention.
Figure 8:
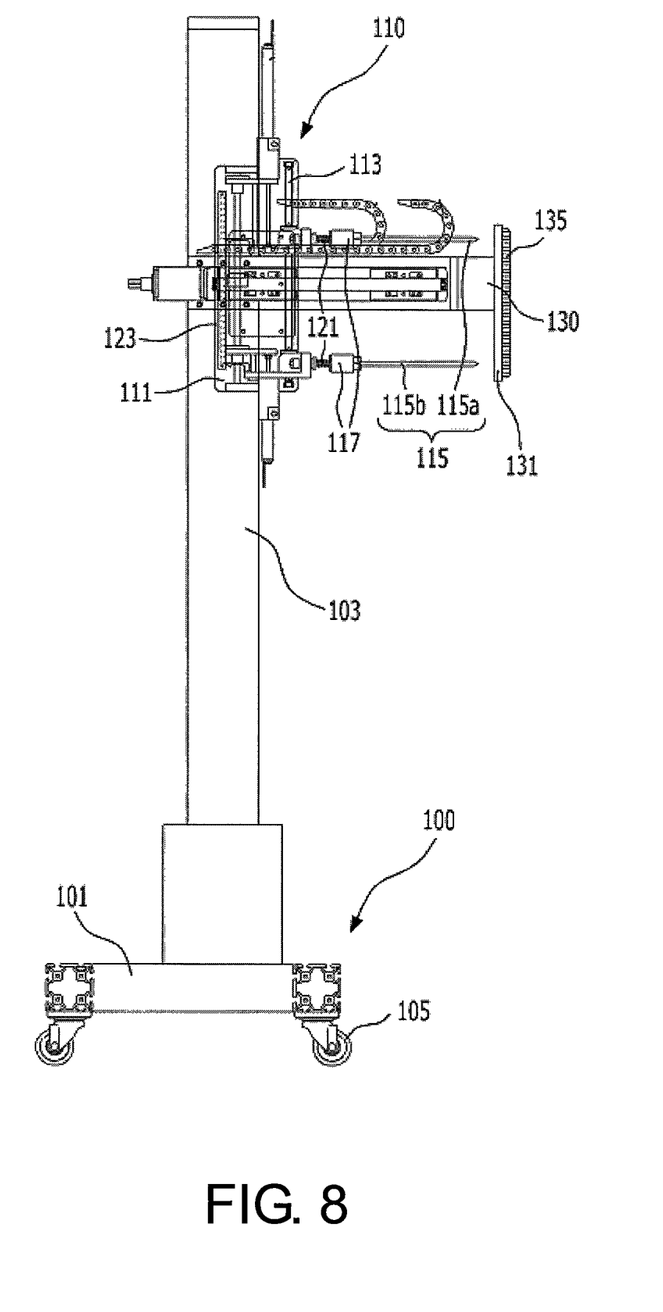
FIG. 8 is a side view of FIG. 7.

As shown in FIG. 7, the elongation measurement unit 100 is movably disposed at one side of the high temperature tension unit 10. More specifically, as shown in FIG. 4, the elongation measurement unit 100 may be installed at one side of the heater 50 of the high temperature tension unit 10 to measure elongation of the tensed test sample in the heater body 51.

The elongation measurement unit 100 includes a movable frame 101 configured to be movable by a plurality of rollers 105, etc. In addition, a vertical bar 103 is installed at the movable frame 101 to vertically extend therefrom.

A measurement head part 100 is connected to the vertical bar 103 to vertically move along the vertical bar 103 to measure elongation of the test sample. The measurement head part 110 includes a head body 111 movable along a vertical guide rail 113 installed at the vertical bar 103 in a vertical direction.

A measurement bar 115 connected to the head body 111 and horizontally extending from the head body 111 is configured to move in a vertical direction.

The measurement bar 115 includes an upper measurement bar 115*a* and a lower measurement bar 115*b*. After the upper measurement bar 115*a* and the lower measurement bar 115*b* contact one surface of the test sample t, when the test sample t is tensed to measure a moved state of the measurement bar 115, elongation of the test sample t can be measured on the basis of a strained length, etc., of the test sample t.

While the lower measurement bar 115*b* is fixed to the vertical guide rail 113, the lower measurement bar 115*b* is fixedly connected to allow slight vertical separation from the vertical guide rail 113. In addition, the upper measurement bar 115*a* is freely movable in a vertical direction.

The measurement bar 115 includes a cooler 117 for cooling heat applied to the measurement bar 115. The cooler 117 is connected to a supply pipe 119 through which cooling water is supplied from the exterior.

Therefore, the measurement bar 115 is cooled by the cooling water supplied through the supply pipe 119 to prevent damage or deformation of the apparatus due to the heat applied from the heater 50.

In addition, the cooler 117 includes a shock-absorbing part 121 to bring the measurement bar 115 in close contact with the test sample. The shock-absorbing part 121 may be formed of a spring member to bring the measurement bar 115 in close contact with the test sample t.

Further, the head body 111 includes a measurement scale 123 for measuring a moving distance of the measurement bar 115 with the naked eye. While all components of the head body 111 are electronically controlled and a moving distance and position of each component are electronically checked and controlled, the moving distance of the measurement bar 115 may be recognized through the measurement scale 123 with the naked eye.

A guide bar 130 extending in a horizontal direction is connected to the head body 110. The guide bar 130 extends in a horizontal direction to guide the measurement bar 115 to the high temperature tension unit 10. The guide bar 130 is configured to vertically move along the head body 111.

Figure 9:
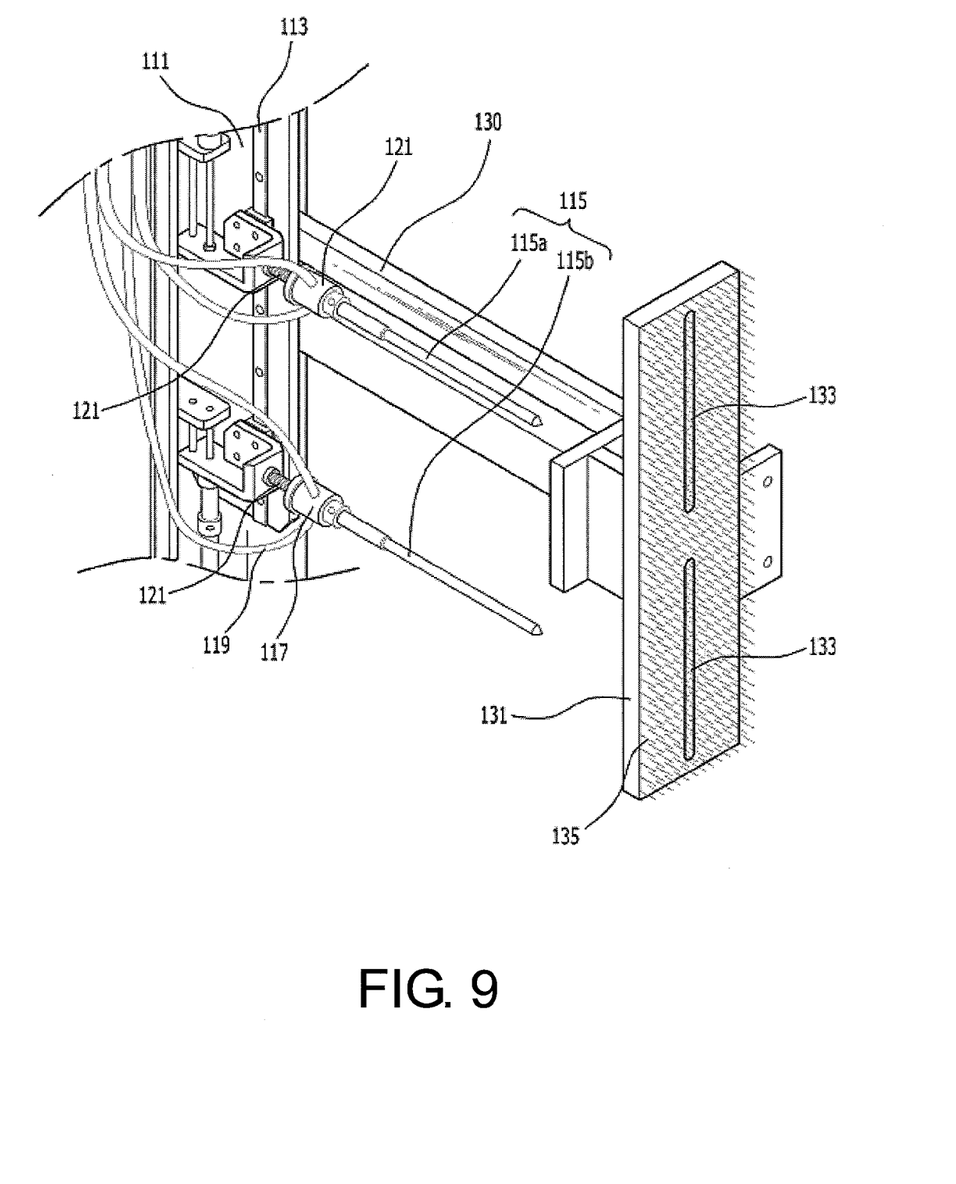
FIG. 9 is an enlarged perspective view of a measurement head of the unit for measuring elongation in accordance with the present invention.

A guide plate 131 is installed at a front end of the guide bar 130 to provide a surface opposite to the high temperature tension unit 10. As shown in FIG. 9, the guide plate 131 has a guide slit 133 cut in a vertical direction thereof.

The measurement bar 115 passes through the guide slit 133 and the insertion slit 61 of the heater body 51 to be in close contact with one end of the test sample, testing elongation of the test sample.

The guide plate 131 includes a heat blocking part 135 for blocking heat from the heater 50. The heat blocking part 135 may be formed of a non-combustible fiber or a fireproof fiber.

Hereinafter, operations of the apparatus for testing a tensile strength under a high temperature condition and a unit for measuring elongation provided in the same in accordance with the present invention will be described in detail.

First, in consideration of the length, etc., of the test sample t, an installation position of the fixing mount 25 of the high temperature tension unit 10 is set. Then, after positioning the heater body 51 between the upper test sample loader 31*a* and the lower test sample loader 31*b*, as shown in FIG. 5, the heater body 51 is separated into left and right halves.

Next, the test sample t is fixed to the vice part 33 of the test sample loader 31, and the heater body 51 is coupled to the test sample t and fixed by the connection clip 53.

When the test sample t is fixed, the elongation measurement unit 100 is disposed at a side of the high temperature tension unit 10. The measurement bar 115 installed at the elongation measurement unit 100 is in close contact with one end of the test sample t and fixed thereto through the guide slit 133 of the guide plate 131 and the insertion slit 61 of the heater body 51.

Next, the test sample t is tensed while being heated by the heater 50, so that a tensile strength and elongation under a high temperature condition can be measured.

A method of heating the test sample t using the heater 50 may be performed according to various fire curves. Important fire curves generally used in the fire test may include ISO, Hydrocarbon, RWS, Modified Hydrocarbon Temperature Curves, and so on.

The ISO Temperature Curve, a standard fire curve, has no limit in fire continuation time and a maximum temperature of 1000° C. The Hydrocarbon Temperature Curve is a curve applied to a situation such as an oil fire, has a fire load of 200 kw/m$^2$, and uses a hydrocarbon curve to a maximum temperature of 1100° C.

In addition, the RWS Temperature Curve is a fire curve using a fire scenario generated under a condition of a fire load of 300 MW, and has a fire continuation time of 120 minutes. A temperature of the fire arrives at 1100° C. within five minutes, arrives at a maximum temperature of 1350° C. after one hour, and then maintains 1200° C. after two hours.

The Modified Hydrocarbon Temperature Curve, which is modified by a temperature increase ratio, is a fire curve for analyzing thermal impact effects on a material upon an initial abrupt temperature increase under a fire load condition of 345 kw/m$^2$. A temperature of the fire arrives at 1100° C. within five minutes, and then arrives at a maximum temperature of 1300° C. after one hour.

The test sample t may be tensed while applying heat on the basis of the fire curves, the test sample t may be tensed after applying heat to a certain temperature, or the test sample t may be heated in a state in which the test sample t is tensed to some extent.

When the test sample t is tensed, the measurement bar 115 of the elongation measurement unit 100 is also vertically moved according to a strained level of the test sample t. Accordingly, it is possible to measure a tensile force and elongation of the test sample t according to a moving distance of the measurement bar 115.

In addition, while heat is applied to the test sample t, the heat is primarily blocked by the heat blocking part 135 of the elongation measurement unit 100, and secondarily blocked by the cooler 117 of the elongation measurement unit 100, preventing damage to and deformation of the apparatus due to the heat.

While it has been described in the present invention that the elongation measurement unit is separately provided from the high temperature tension unit, the elongation measurement unit may be integrally provided in the high temperature tension unit.

In addition, the apparatus for testing a tensile strength in a high temperature condition can not only apply a tensile force to a test sample but also operate the test sample loader in an opposite direction to provide a compression force to the test sample.

The apparatus for testing a tensile strength under a high temperature condition and the unit for measuring elongation provided in the same in accordance with the present invention have the following advantages.

Since a tensile strength and elongation of a test sample can be measured by a heater for forming a high temperature condition on the basis of various fire curves, it is possible to recognize deformation characteristics of materials due to fires to design fireproof structures and equipment.

In addition, since deformation of and damage to the elongation measurement unit due to heat can be prevented by the cooler and the heat blocking part even under a high temperature to condition, it is possible to improve durability and reliability of the apparatus.

As apparent from the above description, according to the apparatus for testing a tensile strength under a high temperature condition and a unit for measuring elongation provided in the same in accordance with the present invention, since a tensile strength and elongation of a test sample can be measured by a heater for forming a high temperature condition on the basis of various fire curves, it is possible to recognize deformation characteristics of materials due to fires to design fireproof structures and equipment, and since deformation of and damage to the elongation measurement unit due to heat can be prevented by the cooler and the heat blocking part even under a high temperature condition, it is possible to improve durability and reliability of the apparatus.

It will be apparent to those skilled in the art that various modifications and variations can be made in the present invention without departing from the spirit or scope of the invention. Thus, it is intended that the present invention covers the modifications and variations of this invention provided they come within the scope of the appended claims and their equivalents.

What is claimed is:

1. An apparatus for testing a tensile strength under a high temperature condition, which measures a tensile strength or elongation of a test sample, comprising:

a high temperature tension unit for applying a tensile force to the test sample and selectively forming a high temperature condition to the test sample; and an elongation measurement unit integrally or separately formed with the high temperature tension unit to measure elongation of the test sample by the high temperature tension unit, wherein the high temperature tension unit comprises:

a base frame part including a surface plate, four support masts extending upward from the surface plate, and a fixing mount connected to the support masts to move vertically along the support masts;

a tensile force applying part connected to the base frame part and applying a tensile force to the test sample; and a heater connected to the base frame part and forming a high temperature condition to the test sample.

2. The apparatus for testing a tensile strength in a high temperature condition according to claim 1, wherein the tensile force applying part comprises a test sample loader having an upper test sample loader connected to the fixing mount and a lower test sample loader connected to the surface plate and fixing and tensing the test sample between the upper and lower test sample loaders, and a cylinder part for moving the test sample loader.

3. The apparatus for testing a tensile strength in a high temperature condition according to claim 1, wherein the heater comprises:

a heater body connected to the base frame part and formed to pass the test sample therethrough;

a plurality of hot-wires installed in the heater body; and a heat blocking material installed in the heater body and limiting discharge of the heat to the exterior.

4. The apparatus for testing a tensile strength in a high temperature condition according to claim 3, wherein the heater body is pivotally connected to the base frame part and configured to be separated into left and right halves, and has an insertion slit through which a measurement bar is inserted to measure elongation of the test sample.

5. A unit for measuring elongation, which is provided in an apparatus for measuring a tensile strength or elongation of a test sample under a high temperature condition, comprising:

a movable frame;

a vertical bar extending upward from the movable frame; and a measurement head part vertically movably connected to the vertical bar, and configured to measure elongation of the test sample and prevent transfer of heat to the movable frame or the vertical bar.

6. The unit for measuring elongation according to claim 5, wherein the measurement head part comprises:

a head body vertically movably connected to the vertical bar;

two measurement bars vertically movably connected to the head body and contacting the test sample;

a cooler installed at the measurement bar and cooling the measurement bars using cooling water supplied from the exterior; and a guide bar installed at the measurement head part and having a heat blocking part formed of a non-combustible fiber or a fireproof fiber to block heat applied to the measurement head part.

* * * * *